United States Patent
Kohlmann

(10) Patent No.: US 10,851,159 B2
(45) Date of Patent: Dec. 1, 2020

(54) ANTIBODIES THAT BIND TO HUMAN ANTI-MÜLLERIAN HORMONE (AMH) AND THEIR USES

(71) Applicant: Angelica Kohlmann, Zürich (CH)

(72) Inventor: Angelica Kohlmann, Zürich (CH)

(73) Assignee: Bloom Diagnostics AG, Zürich (CH)

( * ) Notice: Subject to any disclaimer, the term of this patent is extended or adjusted under 35 U.S.C. 154(b) by 0 days.

(21) Appl. No.: 16/306,489

(22) PCT Filed: Jun. 1, 2017

(86) PCT No.: PCT/EP2017/063312
§ 371 (c)(1),
(2) Date: Nov. 30, 2018

(87) PCT Pub. No.: WO2017/207694
PCT Pub. Date: Dec. 7, 2017

(65) Prior Publication Data
US 2019/0330331 A1  Oct. 31, 2019

(30) Foreign Application Priority Data
Jun. 2, 2016  (EP) .................................... 16172695

(51) Int. Cl.
*C07K 16/26* (2006.01)
*A61P 35/00* (2006.01)
*A61K 39/00* (2006.01)

(52) U.S. Cl.
CPC .............. *C07K 16/26* (2013.01); *A61P 35/00* (2018.01); *A61K 2039/505* (2013.01); *C07K 2317/24* (2013.01); *C07K 2317/73* (2013.01); *C07K 2317/92* (2013.01)

(58) Field of Classification Search
None
See application file for complete search history.

(56) References Cited

U.S. PATENT DOCUMENTS 5,661,126 A * 8/1997 Donahoe ............... A61K 48/00
435/68.1
9,458,239 B2 * 10/2016 Teulon .................. C07K 16/28

OTHER PUBLICATIONS

Strausberg et al., PNAS, 2002; 99: 16899-16903 (Year: 2002).*
Piche-Nicholas et al., MAbs. 2018; 10: 81-94. doi: 10.1080/19420862.2017.1389355 (Year: 2018).*
Gowkielewicz et al., Int. J. Mol. Sci. 2019, 20, 1325 (Year: 2019).*
Kersual et al., "The human Müellerian inhibiting substance type II receptor as immunotherapy target for ovarian cancer," *mAbs* 6(5):1314-1326.
Lefevre et al., "Anti-idiotypic antibodies to a monoclonal antibody raised against anti-Müellerian hormone exhibit anti-Müellerian biological activity," *Mol Cell Endocrinol* 62(1):125-133 (1989).
Mamsen et al., "Proteolytic processing of anti-Müellerian hormone differs between human fetal testes and adult ovaries," *Mol Hum Reprod* 21(7):571-582 (2015).
Mus musculus immunoglobulin kappa chain complex mRNA (cDNA clone MGC:6612 IMAGE:3488780), complete cds, GENBANK ID BC002112.1, dated Mar. 18, 2009. Retrieved from <https://www.ncbi.nlm.nih.gov/nuccore/BC002112> on Nov. 11, 2014.
Pepin et al., "AAV9 delivering a modified human Mullerian inhibiting substance as a gene therapy in patient-derived xenografts of ovarian cancer," *Proc Nat Acad Sci USA* 112(32):E4418-E4427 (2015).
Weenen et al., "Anti-Müellerian hormone expression pattern in the human ovary: potential implications for initial and cyclic follicle recruitment," *Mol Hum Reprod* 10(2):77-83 (2004).
International Search Report dated Aug. 14, 2017 in corresponding International Patent Application No. PCT/EP2017/063312.

* cited by examiner

*Primary Examiner* — Christina M Borgeest
(74) *Attorney, Agent, or Firm* — Medler Ferro Woodhouse & Mills PLLC

(57) ABSTRACT

The present invention relates to antibodies or fragments thereof that bind to human Anti-Müllerian hormone (AMH) comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6. The present invention further relates to antibodys or fragments thereof that bind to human Anti-Müllerian hormone (AMH) for use in a method for treating cancer in a subject.

13 Claims, 4 Drawing Sheets
Specification includes a Sequence Listing.

ANTIBODIES THAT BIND TO HUMAN ANTI-MÜLLERIAN HORMONE (AMH) AND THEIR USES

REFERENCE TO AN ELECTRONIC SEQUENCE LISTING

The contents of the electronic sequence listing (0192-0076US1 SL.txt; Size: 20,480 bytes; and Date of Creation Nov. 20, 2018) is herein incorporated by reference in its entirety.

THE FIELD OF THE INVENTION

The present invention relates to antibodies or fragments thereof that bind to human Anti-Müllerian hormone (AMH) comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6. The present invention further relates to antibodies or fragments thereof that binds to human Anti-Müllerian hormone (AMH) for use in a method for treating cancer in a subject.

BACKGROUND OF THE INVENTION

Anti-Mullerian Hormone or Anti-Müllerian Hormone (AMH), also referred to as Mullerian or Müllerian inhibiting factor (MIF), Mullerian-inhibiting hormone or Müllerian-inhibiting hormone (MIH), and Mullerian-inhibiting substance or Müllerian-inhibiting substance (MIS), is a 140-kilodalton (kDa) dimeric glycoprotein hormone, that is part of the transforming growth factor-P (TGF-P) superfamily (Zec, I. et al., "Anti-Müllerian hormone: A unique biochemical marker of gonadal development and fertility in humans," Biochemica Medica, 21(3):219-30, October 2011).

Before secretion, the mature hormone undergoes glycosylation and dimerization resulting in a 140-kDa dimer of identical, 70-kDa, disulfide-linked, monomer subunits and each monomer has an N-terminal domain (known as the "pro" region) and a C-terminal domain (known as the "mature" region) (Zec, I. et al., "Anti-Müllerian hormone: A unique biochemical marker of gonadal development and fertility in humans," Biochemica Medica, 21(3):219-30, October 2011).

The gene encoding human AMH has been sequenced and isolated, and it is located on the short arm of chromosome 19 (Zec, I. et al., "Anti-Müllerian hormone: A unique biochemical marker of gonadal development and fertility in humans," Biochemica Medica, 21(3):219-30, October 2011). The amino acid sequence of human AMH has the sequence database accession number P03971 (Uniprot) and is shown in SEQ ID NO: 9.

AMH plays an important role in sexual differentiation. AMH is produced by the Sertoli cells of the testis in the male, and by ovarian granulosa cells in the female. In males, AMH is responsible for the regression of the Müllerian ducts that would differentiate into the female oviducts, uterus and the upper portion of the vagina. In males, secretion of AMH by the Sertoli cells commences during embryogenesis and continues throughout life. From birth to puberty, AMH remains secreted at high levels. In females AMH is expressed in ovarian granulosa cells and is present prior to birth, before menarche, and throughout the reproductive years. Later, in adult women, it is a molecular biomarker for the ovarian cell reserve and overall remaining fertility. Since a few years, AMH also became an early marker for relapse/metastasis after the treatment of ovarian cancer. As AMH is an inhibiting protein studies followed suggesting AMH could prove effective as a co-adjuvant therapy during chemotherapy in the treatment of ovarian cancer (Pépin et al. Harvard Medical School PNAS Published online Jul. 27, 2015).

Since current therapies such as chemotherapy in the treatment of cancer of organs of the male and female reproductive systems have severe side effects there exists a need to develop therapies that are more effective and more specific to treat cancer of e.g. organs of the male and female reproductive system. Surprisingly, it has been found that antibodies that bind to AMH cause higher survival rate in subjects having cancer of organs of the male and female reproductive systems such as ovarian cancer.

SUMMARY OF THE INVENTION

The present disclosure relates generally to antibodies or fragments thereof that bind to human Anti-Müllerian hormone (AMH), methods for their preparation and use, including methods for treating cancer.

In one aspect, the present disclosure provides an antibody or fragment thereof that binds to human Anti-Müllerian hormone (AMH) comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6.

In a further aspect the present invention provides an antibody or fragment thereof that binds to human AMH, wherein the antibody or fragment thereof comprises a heavy chain variable region of SEQ ID NO: 7 and/or a light chain variable region sequence of SEQ ID NO: 8.

In a further aspect the present invention provides an antibody or fragment thereof that binds to human AMH wherein the antibody or fragment thereof comprises a heavy chain variable framework region sequence which is at least 70% identical to the framework region sequence of SEQ ID NO: 7 and/or a light chain variable framework region sequence which is at least 70% identical to the framework region sequence of SEQ ID NO: 8.

In a further aspect the present invention provides an antibody or fragment thereof that binds to human AMH, wherein the antibody or fragment thereof is a murine antibody or a fragment thereof, a chimeric antibody or a fragment thereof or a humanized antibody or fragment thereof.

In a further aspect the present invention provides an antibody or fragment thereof that binds to human AMH with an affinity ($K_d$) of 10 nM or less.

The present disclosure also provides compositions comprising the antibody or fragment thereof and a pharmaceutically acceptable carrier. The present disclosure also provides methods for treating cancer and methods of inhibiting growth of tumor cells. The present disclosure also provides kits and articles of manufacturing comprising the antibody or fragment thereof that binds to human AMH.

DETAILED DESCRIPTION OF THE INVENTION

Figure 1:
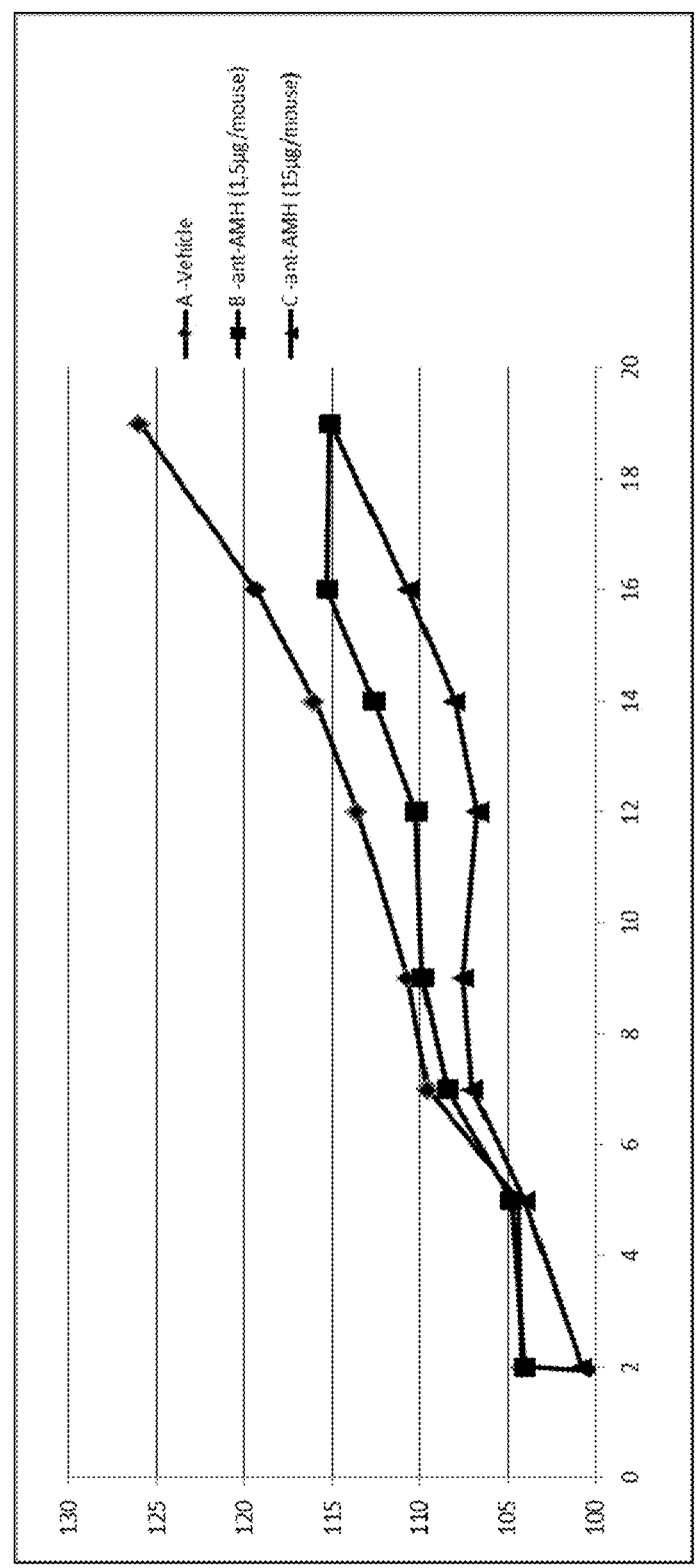
FIG. 1 shows body weight change [%] of mice bearing Ovcar-3 cells treated with anti-AMH antibody.

The present disclosure relates to antibodies or fragments thereof that bind to human Anti-Müllerian hormone (AMH) and methods for treating cancer using antibodies or fragments thereof that bind to human AMH.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting. The terms "comprising", "having", and "including" are to be construed as open-ended terms (i.e., meaning "including, but not limited to") unless otherwise noted.

The term "human AMH" as used herein includes variants, isoforms, and species homologs of human AMH. Accordingly, antibodies of this disclosure may, in certain cases, cross-react with AMH from species other than human. In certain embodiments, the antibodies may be completely specific for one or more human AMH proteins and may not exhibit species or other types of non-human cross-reactivity. The complete amino acid sequence of an exemplary human AMH protein is shown in SEQ ID NO: 9. The use of "human AMH" herein encompasses all known or as yet undiscovered alleles and polymorphic forms of human AMH. The term "AMH" as used herein refers to "human AMH" if not otherwise specifically indicated.

The term "antibody that bind to human AMH" as used herein includes antibodies, preferably IgG antibodies, more preferably IgG1 antibodies that bind to human AMH e.g. that bind to recombinant human AMH as shown in SED ID NO: 10 as provided in a sandwhich immunoassay to the antibodies, with an affinity (Kd) of 50 nM or less, preferably 10 nM or less, more preferably 5 nM or less, in particular 1 nM or less.

The term "antibody" as referred to herein includes whole antibodies i.e. full length antibodies and any antigen binding fragment or single chains thereof. An "antibody" refers to a glycoprotein comprising at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CHI, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR or FW). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the First component (C1q) of the classical complement system. Preferably the antibody of the present invention is a full length antibody.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (C[gamma]2 and C[gamma]3) and the hinge between Cgamma1 (C[gamma]1) and Cgamma2 (C[gamma]2). Although the boundaries of the Fc region may vary, the human IgG heavy chain Fc region is usually defined to comprise residues C226 or P230 to its carboxyl-terminus, wherein the numbering is according to the EU index as in Kabat. For human IgG1 the Fc region is herein defined to comprise residue P232 to its carboxyl-terminus, wherein the numbering is according to the EU index as in Kabat. Fc may refer to this region in isolation, or this region in the context of an Fc polypeptide, for example an antibody.

The term "hinge" or "hinge region" or "antibody hinge region" herein includes the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgGl) to 231 (A231 in IgGI), wherein the numbering is according to the EU index as in Kabat.

The term "parent antibody" or "parent immunoglobulin" as used herein includes an unmodified antibody that is subsequently modified to generate a variant. Said parent antibody may be a naturally occurring antibody, or a variant or engineered version of a naturally occurring antibody.

Parent antibody may refer to the antibody itself, compositions that comprise the parent antibody, or the amino acid sequence that encodes it. By "parent anti-AMH antibody" as used herein is meant an antibody or immunoglobulin that binds human AMH and is modified to generate a variant.

The term "parental antibody" or "parental immunoglobulin" as used herein includes a murine or chimeric antibody that is subsequently modified to generate a humanized antibody.

The term "variant antibody" or "antibody variant" as used herein includes an antibody sequence that differs from that of a parent antibody sequence by virtue of at least one amino acid modification compared to the parent. The variant antibody sequence herein will preferably possess at least about 70%, more preferably at least about 80%, most preferably at least about 90%, in particular at least about 95% amino acid sequence identity with a parent antibody sequence. Antibody variant may refer to the antibody itself, compositions comprising the antibody variant, or the amino acid sequence that encodes it.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example, R94K/L78V refers to a double variant comprising the substitutions R94K and L78V. By "amino acid insertion" or "insertion" as used herein is meant the addition of an amino acid at a particular position in a parent polypeptide sequence. For example, insert −94 designates an insertion at position 94. By "amino acid deletion" or "deletion" as used herein is meant the removal of an amino acid at a particular position in a parent polypeptide sequence. For example, R94-designates the deletion of arginine at position 94. The amino acid modification is preferably a conservative sequence modification.

As used herein, the term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions or within the framework regions of an antibody of the invention can be replaced with other amino acid residues from the same side chain family and the altered antibody (variant antibody) can be tested for retained function.

For all human immunoglobulin heavy chain constant domains numbering is according to the "EU numbering system" (Edelman G M et al., (1969) PNAS USA 63(1): 78-85). For the human kappa immunoglobulin light chain constant domain (IGKC), numbering is according to the "EU numbering system" (Edelman G M et al., ibid.). For the human lambda immunoglobulin light chain constant domains (IGLC1, IGLC2, IGLC3, IGLC6, and IGLC7), numbering is according to the "Kabat numbering system" referred herein as "Kabat" or "set forth in Kabat" (Kabat E A et al., (1991) Sequences of proteins of immunological interest. 5th Edition—US Department of Health and Human Services, NIH publication n° 91-3242).

All Complementarity Determining Regions (CDRs) as referred to in the present invention, are defined preferably as follows (numbering according to the numbering system set forth in Kabat): LCDR1: 24-34; LCDR2: 50-56; LCDR3: 89-97; HCDR1: 31-35; HCDR2: 50-66; HCDR3: 99-110.

The heavy chain variable framework region may comprise one or more (e.g., one, two, three and/or four) heavy chain framework region sequences (e.g., framework 1 (FR1), framework 2 (FR2), framework 3 (FR3) and/or framework 4 (FR4)). The heavy chain variable region framework comprises usually FR1, FR2, FR3 and FR4. Preferably the heavy chain variable region framework comprises FR1, FR2 and/or FR3, more preferably FR1, FR2 and FR3.

Heavy chain framework region sequences as used herein comprise the amino acid sequences: FR1 (1-30), FR2 (36-49), FR3 (67-98), and FR4 (111-121), wherein the amino acid position is indicated utilizing the numbering system set forth in Kabat.

The light chain variable region framework region may comprise one or more (e.g., one, two, three and/or four) light chain framework region sequences (e.g., framework 1 (FR1), framework 2 (FR2), framework 3 (FR3) and/or framework 4 (FR4)). The light chain variable region framework comprises usually FR1, FR2, FR3 and FR4. Preferably the light chain variable region framework comprises FR1, FR2 and/or FR3, more preferably FR1, FR2 and FR3. Light chain framework region sequences as used herein comprise the amino acid sequences: FR 1(1-23), FR2 (35-49), FR3 (57-88), and FR4 (98-107), wherein the amino acid position is indicated utilizing the numbering system set forth in Kabat.

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (C[gamma]1), CH2 (C[gamma]2), and CH3 (C[gamma]3). In some mammals, for example in camels and llamas, IgG antibodies may consist of only two heavy chains, each heavy chain comprising a variable domain attached to the Fc region.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (vii) bispecific single chain Fv dimers (PCT/US92/09965), (viii) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448) and (ix) scFv genetically fused to the same or a different antibody (Coloma & Morrison, 1997, Nature Biotechnology 15, 159-163).

Antibodies are grouped into classes, also referred to as isotypes, as determined genetically by the constant region. Human constant light chains are classified as kappa (CK) and lambda (C[lambda]) light chains. Heavy chains are classified as mu, delta, gamma, alpha, or epsilon, and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The term "cancer" refers to or describes the physiological condition in mammals that is typically characterized by unregulated cell growth. Included in this definition are benign and malignant cancers, metastatic cancers as well as adenomas or adenocarcinomas. "Tumor" refers to all neoplastic cell growth and proliferation, whether malignant or benign, and all pre-cancerous and cancerous cells and tissues. "Benign tumor" or "benign cancer" refers to a tumor that remains localized at the site of origin and does not have the capacity to infiltrate, invade, or metastasize to a distant site. "Malignant tumor" refers to a tumor that invades and damages other tissues around them. Treatment of cancer refers to both therapeutic use and prophylactic or preventative use of the AMH antibodies described herein. Those in need of treatment include those already diagnosed with the cancer as well as those in which the onset of the disorder is to be prevented or delayed.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Preferably the subject is human.

Anti-AMH Antibodies

In a first aspect the present invention provides an antibody or fragment thereof that binds to human Anti-Müllerian hormone (AMH) comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6.

Preferably the antibody or fragment thereof that binds to human AMH comprises a heavy chain CDR1 comprising the amino acid sequence of SEQ ID NO: 1, and a heavy chain CDR2 comprising the amino acid sequence of SEQ ID NO: 2, and a heavy chain CDR3 comprising the amino acid sequence of SEQ ID NO: 3; and/or comprises a light chain CDR1 comprising the amino acid sequence of SEQ ID NO: 4, and a light chain CDR2 comprising the amino acid sequence of SEQ ID NO: 5 and a light chain CDR3 comprising the amino acid sequence of SEQ ID NO: 6. More preferably the antibody or fragment thereof that binds to AMH comprises a heavy chain CDR1 comprising the amino acid sequence of SEQ ID NO: 1, and a heavy chain CDR2 comprising the amino acid sequence of SEQ ID NO: 2, and a heavy chain CDR3 comprising the amino acid sequence of SEQ ID NO: 3; and comprises a light chain CDR1 comprising the amino acid sequence of SEQ ID NO: 4, and a light chain CDR2 comprising the amino acid sequence of SEQ ID NO: 5 and a light chain CDR3 comprising the amino acid sequence of SEQ ID NO: 6.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al, British J. of Cancer 83 [pound]2):252-260 (2000) (describing the production of a humanized anti-CD30 antibody using only the heavy chain variable domain CDR3 of murine anti-CD30 antibody Ki-4); Beiboer et al, J. Mol. Biol. 296:833-849 (2000) (describing recombinant epithelial glycoprotein-2 (EGP-2) antibodies using only the heavy chain CDR3 sequence of the parental murine MOC-31 anti-EGP-2 antibody); Rader et al, Proc. Natl Acad. ScL U.S.A. 95:8910-8915 (1998) (describing a panel of humanized anti-integrin [alpha]v[beta]3 antibodies using a heavy and light chain variable CDR3 domain of a murine anti-integrin [alpha]v[beta]3 antibody LM609 wherein each member antibody comprises a distinct sequence outside the CDR3 domain and capable of binding the same epitope as the parental murine antibody with affinities as high or higher than the parental murine antibody); Barbas et al, J. Am. Chem. Soc. 116:2161-2162 (1994) (disclosing that the CDR3 domain provides the most significant contribution to antigen binding).

Accordingly, the present invention provides antibodies or fragments thereof that binds to human AMH comprising one or more heavy and/or light chain CDR3 domains from an antibody of a non-human animal e.g from a murine antibody, in particular comprising heavy chain CDR3 comprising the amino acid sequence of SEQ ID NO: 3 and/or light chain CDR3 comprising the amino acid sequence of SEQ ID NO: 6, wherein the antibody is capable of binding to human AMH. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human e.g. murine antibody.

In a further aspect the present invention provides an antibody or fragment thereof that binds to human AMH, wherein the antibody or fragment thereof comprises a heavy chain variable region of SEQ ID NO: 7.

In a further aspect the present invention provides an antibody or fragment thereof that binds to human AMH, wherein the antibody or fragment thereof comprises a light chain variable region sequence of SEQ ID NO: 8.

In a further aspect the present invention provides an antibody or fragment thereof that binds to human AMH, wherein the antibody or fragment thereof comprises a heavy chain variable region of SEQ ID NO: 7 and a light chain variable region sequence of SEQ ID NO: 8.

In another aspect the present invention provides variants of an antibody or fragment thereof that binds to human AMH. Thus the present invention provides antibodies or fragments thereof that have an amino acid sequence of the heavy and/or light chain variable framework region which is at least 70% identical (having at least 70% amino acid sequence identity) to the amino acid sequence of the heavy and/or light chain variable framework region of the parent antibody of either the heavy or the light chain e.g. of either the heavy and light variable region sequences as in SEQ ID NO: 7 or SEQ ID NO: 8, respectively. Preferably the amino acid sequence identity of the heavy and/or light chain variable framework region is at least 80%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to an amino acid sequence is defined herein as the percentage of amino acid residues in the candidate sequence that are identical with the antibody or fragment thereof that binds to human AMH, after aligning the sequences and introducing gaps, if necessary, to achieve the maximum percent sequence identity. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3 (1978)) can be used in conjunction with the computer program. For example, the percent identity can be calculated as: the total number of identical matches multiplied by 100 and then divided by the sum of the length of the longer sequence within the matched span and the number of gaps introduced into the longer sequences in order to align the two sequences.

In some embodiments the present disclosure thus provides an antibody or fragment thereof that binds to human AMH, wherein the antibody or fragment thereof comprises a heavy chain variable framework region sequence which is at least 70% identical to the framework region sequence of SEQ ID NO: 7 and/or a light chain variable framework region sequence which is at least 70% identical to the framework region sequence of SEQ ID NO: 8.

In another aspect, the present disclosure also provides an antibody or fragment thereof that binds to human AMH, wherein at least one of the heavy chain CDRs and/or at least one of the light chain CDRs comprises at least one amino acid modification. Site-directed mutagenesis or PCR-mediated mutagenesis can be performed to introduce the modification(s) and the effect on antibody binding, or other functional property of interest, can be evaluated in in vitro or in vivo assays. Preferably conservative modifications are introduced. The modification(s) may be amino acid substitutions, additions or deletions, but are preferably substitutions. Typically, no more than five, preferably no more than four, more preferably no more than three, even more preferably no more than two, most preferably no more than one amino acid modifications are performed within a CDR region.

The present disclosure also provides an antibody or fragment thereof that binds to human AMH which further comprises a human heavy and/or light constant domain. Human heavy constant regions may be selected from the group of human immunoglobulins consisting of IgG1, IgG2, IgG3, IgG4, IgA1, IgA2, IgM1, IgM2, IgD, and IgE, whereas the human heavy constant region IgG, in particular IgG1 is preferred. Human light constant region may be selected from the group of human immunoglobulins consisting of kappa or lambda constant regions, whereas human kappa constant region is preferred. In some preferred embodiments the antibody or fragment thereof comprises a human IgG1 heavy constant domain and a human light kappa constant domain. The present disclosure also provides an antibody or fragment thereof that binds to human AMH comprising human heavy and/or light constant regions, wherein the human heavy constant region comprises an isotypic variant comprising the CH1 from human IgG1, the hinge from human IgG1 and the Fc region from human IgG3.

The present disclosure also provides a fragment of an antibody that binds to human AMH selected from the group consisting of Fab, Fab', Fab'-SH, Fd, Fv, dAb, F(ab')2, scFv, bispecific single chain Fv dimers, diabodies, triabodies and scFv genetically fused to the same or a different antibody. Preferred fragments are scFv, bispecific single chain Fv dimers and diabodies. The present disclosure also provides a full length antibody that binds to human AMH.

In one embodiment the antibody or fragment thereof is a murine antibody or a fragment thereof, a chimeric antibody or a fragment thereof or a humanized antibody or fragment thereof. In one embodiment the antibody or fragment thereof is a monoclonal antibody.

Anti-AMH Antibodies Properties

Standard assays to evaluate the binding ability of the antibodies toward e.g. human AMH are known in the art, including for example, ELISAs, Western blots, RIAs, and flow cytometry analysis. Suitable assays are described in detail in the Examples. The binding kinetics (e.g., binding affinity like $K_d$) of the antibodies also can be assessed by standard assays known in the art, such as by Surface Plasmon Resonance (SPR) measurements and/or by Scatchard or Biacore® system analysis and can be performed and calculated e.g. as described in Example 1. The relative binding affinity $K_i$ can be assessed by standard competion assay known in the art.

The present disclosure provides an antibody or fragment thereof that binds to human AMH with an affinity ($K_d$) of 50 nM or less, preferably 10 nM or less, more preferably 5 nM or less, in particular 1 nM o less.

Nucleic Acids, Vectors and Host Cells

Nucleic acids of the antibodies of the present invention can be obtained using standard molecular biology techniques e.g. cDNAs encoding the light and heavy chains of the antibody or encoding VH and VL segments can be obtained by standard PCR amplification or cDNA cloning techniques. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g. F. Ausubel, et al, ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Once DNA fragments encoding VH and VL segments are obtained, these DNA fragments can be further manipulated by standard recombinant DNA techniques, for example to convert the variable region genes to full-length antibody chain genes, or to fragments genes corresponding to the fragments described supra like Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 constant region. For a Fab fragment heavy chain gene, the V[pi]-encoding DNA can be operatively linked to another DNA molecule encoding only the heavy chain CH1 constant region. The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region, preferably a kappa constant region. To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. ScL USA 85:5879-5883; McCafferty et al, (1990) Nature 348: 552-554). Various techniques have been developed for the production of antibody fragments of antibodies. Traditionally, these fragments were derived via proteolytic digestion of intact antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')2 fragments (Carter et al., Bio/Technology, 10: 163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv), see e.g. WO 1993/16185; U.S. Pat. Nos. 5,571,894; and 5,587,458. The antibody fragment may also be a "linear antibody", e.g., as described in U.S. Pat. No. 5,641,870, for example.

The nucleic acids that encode the antibodies of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

Suitable host cells for cloning or expressing the DNA in vectors are prokaryote, yeast, or higher eukaryote cells. Suitable prokaryotes for this purpose include eubacteria, including gram-negative or gram-positive organisms, for example, Enterobacteriaceae such as *Escherichia*, e.g., *E. coli, Enterobacter, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *F. coli* W3110 (ATCC 27,325).

In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful, such as *Schizosaccharoriyces pombe; Kluyveromyces* hosts including *K. lactis, K. fragilis* (ATCC 12,424), *K. bulgaricus* (ATCC 16,045), *K. wickeramii* (ATCC 24,178), *K. WaltH* (AJCC 56,500), *K. drosopmarum* (ATCC 36,906), *K. thermotolerans*, or *K. marxianusyarrowia* (EP 402226); *Pichia pastoris* (EP 183,070); *Candida; Trichoderma* reesia (EP 244234); *Neurospora crassa; Schwanniomyces* such as *Schwanniomyces occidentalis*; and filamentous fungi including *Neurospora, Penicillium, Tolypocladium,* or *Aspergillus* hosts such as *A. nidulans* or *A. niger*. Suitable host cells for the expression of the antibodies of the invention are derived from multicellular organisms. Examples of invertebrate cells include plaril and insect cells. Numerous baculoviral strains and variants and corresponding permissive insect host cells from hosts such as *Spodoptera frugiperda* (caterpillar), *Aedes augypti* (mosquito), *Aedes albopictus* (mosquito), *Drosophila melanogaster* (fruitfly), and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells. Plant cell cultures of cotton, corn, potato, soybean, *petunia*, tomato, and tobacco can also be utilized as hosts.

Host cells for expressing recombinant antibodies are preferably mammalian host cells which include Chinese Hamster Ovary (CHO cells) (including dhfr<->CHO cells, described in Urlaub and Chasin, (1980) Proc. Natl. Acad. ScL USA 77:4216-4220, used with a DHFR selectable marker, e.g., as described in R. J. Kaufman and P. A. Sharp (1982) J. Mol. Biol 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338841 (to Bebbington). When recombinant antibody genes are introduced into mammalian host cells, the antibodies are produced by culturing the host cells for a period of time sufficient to allow for expression of the antibody in the host cells or, more preferably, for secretion of the antibody into the culture medium in which the host cells are grown. Host cells useful for producing antibodies that bind to human AMH may be cultured in a variety of media. Commercially available media such as Ham's F10 (Sigma), Minimal Essential Medium ((MEM), (Sigma), RPMI-1640 (Sigma or Chemie Brunschwig AG, PAA, Basel, Switzerland), and Dulbecco's Modified Eagle's Medium ((DMEM), Sigma) are suitable for culturing the host cells. Antibodies can be recovered from the culture medium using standard protein purification methods.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. Ni<+2>affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both.

Construction and Production of Antibodies

Antibodies can be produced by recombinant DNA techniques known to the skilled person. In addition antibodies can be produced by enzymatic or chemical cleavage of naturally occurring antibodies. Humanized antibodies may be constructed by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for decreasing immunogenicity of the antibody and/or maintaining binding affinity. Optionally, non-human amino acid residues present in the CDRs may be replaced with human residues. Chimeric or humanized antibodies can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al).

Humanized antibodies may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region elude homology in CDR length between the murine donor molecule and the human acceptor molecule. Human acceptor antibody molecules are preferably selected by homology search to the V-BASE database, although other databases such as the Kabat and the public NCBI databases may be used as well.

Humanized antibodies may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. Methods for humanizing a nonhuman antibody are described herein, including in the Examples below.

The present invention provides a method of producing an antibody or fragment thereof that binds to human AMH comprising culturing a host cell comprising an isolated nucleic acid encoding the antibody or fragment thereof that binds to human AMH or a vector comprising an isolated nucleic acid encoding the antibody or fragment thereof that binds to human AMH so that the nucleic acid is expressed and the antibody produced. Preferably the antibody is isolated.

As host cells, nucleic acids and vectors, the ones described supra can be used. Expression of the nucleic acids can be obtained by, for example, a combination of recombinant DNA techniques and gene transfection methods as is well known in the art (e.g., Morrison, S. (1985) Science 229:1202) and as further outlined supra. For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into vectors such as expression vectors. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VK segment is operatively linked to the CL segment within the vector.

Characterization and Purification of Anti-AMH Antibodies.

Antibodies of the invention can be tested for binding to human AMH by, for example, standard ELISA. Antibodies of the present invention may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. To purify anti-AMH antibodies, selected host cells can be grown in e.g spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity.

Immunoconjugates

In another aspect, the present invention provides an anti-AMH antibody or a fragment thereof that binds to human AMH, linked to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be linked to an antibody of the invention include duocarmycins, calicheamicins, maytansines and auristatins, and derivatives thereof. An example of a calicheamicin antibody conjugate is commercially available (Mylotarg®; American Home Products). Cytotoxins can be linked to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55: 199-215; Trail, P. A. et al. (2003) Cancer Immunol. Immunother. 52: 328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3: 1089-1091; Senter, P. D. and Springer, C J. (2001) Adv. Drug Deliv. Rev. 53: 247-264. Antibodies of the present invention also can be linked to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine<131>, indium<111>, yttrium<90> and lutetium<177>. Methods for preparing radioimmunconjugates are established in the art. Examples of radioimmunoconjugates are commercially available, including Zevalin® (EDEC Pharmaceuticals) and Bexxar® (Corixa Pharmaceuticals), and similar methods can be used to prepare radioimmunoconjugates using the antibodies of the invention. The antibody immunoconjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-[gamma]; or, biological response modifiers such as, for example, lymphokines, interleukin-1 ("IL-1"), interleukin-2 ("IL-2"), interleukin-6 ("IL-6"), granulocyte macrophage colony stimulating factor ("G M-CSF"), granulocyte colony stimulating factor ("G-CSF"), or other growth factors.

Techniques for linking such therapeutic agents to antibodies are well known, see, e.g., Amon et al, "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al, "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al, Immunol. Rev., 62: 119-58 (1982).

Pharmaceutical Compositions

In another aspect, the present invention provides a composition, e.g., a pharmaceutical composition, comprising the antibody or fragment thereof, of the present invention, and a pharmaceutically acceptable carrier. Such compositions may include one or a combination of (e.g., two or more different) antibodies or immunoconjugates of the invention. For example, a pharmaceutical composition of the invention can comprise a combination of antibodies (or immunoconjugates) that bind to different epitopes on the target antigen or that have complementary activities. Pharmaceutical compositions of the invention also can be administered in combination therapy, i.e., combined with other agents. For example, the combination therapy can include an anti-AMH antibody of the present invention combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, intraperitoneal, spinal or epidermal administration (e.g., by injection or infusion). Depending on the route of administration, the active compound, i.e., antibody or immunoconjugate, may be coated in a material to protect the compound from the action of acids and other natural conditions that may inactivate the compound. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

In another aspect, the present invention provides a composition comprising an immunoconjugate comprising the antibody or fragment thereof that binds to human AMH linked to a therapeutic agent and a pharmaceutically acceptable carrier. Immunoconjugates and therapeutic agents which can be used are as described supra.

A pharmaceutical composition of the invention may also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic-acid (EDTA), sorbitol, tartaric acid, phosphoric acid, and the like. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic Uses

The antibodies of the present invention have in vitro and in vivo therapeutic utilities involving the prevention and treatment of cancers. For example, these molecules can be administered to cells in culture, in vitro or ex vivo, or to human subjects, e.g., in vivo, to treat, and/or prevent a variety of cancers. Preferred subjects are human and include patients having cancer. The methods are particularly suitable for treating human patients having a cancer selected from the group consisting of breast cancer and cancer of organs of the male and female reproductive systems.

A "patient" for the purposes of the present invention includes both humans and other animals, preferably mammals and most preferably humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease. As another example, successful administration of an antibody after clinical manifestation of the disease to combat the symptoms of the disease comprises treatment of the disease. "Treatment" and "treating" also encompasses administration of an antibody after the appearance of the disease in order to eradicate the disease. Successful administration of an antibody after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In a particular embodiment, the antibodies are used in vivo to treat or prevent a variety of cancers. Thus the invention provides an antibody or fragment thereof that binds to human Anti-Müllerian hormone (AMH) for use in a method for treating cancer in a subject. The invention further provides the use of an antibody or fragment thereof that binds to human AMH for the manufacture of a medicament for treating cancer in a subject.

The invention further provides a method for treating cancer in a subject, the method comprising administering to the subject a therapeutically effective amount of an antibody or fragment thereof that binds to human AMH.

Furthermore, given the expression of AMH by various tumor cells, the cancer is preferably a cancer characterized by the presence of tumor cells expressing AMH. Thus in a further aspect the present invention provides an antibody or fragment thereof that binds to human Anti-Müllerian hormone (AMH) for use in a method of inhibiting growth of tumor cells of breast cancer and/or of tumor cells of organs of the male and female reproductive systems, comprising contacting the tumor cells with the antibody or fragment thereof. The invention further provides a method of inhibiting growth of tumor cells of breast cancer and/or of tumor cells of organs of the male and female reproductive systems, comprising contacting the tumor cells with an antibody or fragment thereof that binds to human AMH. The invention further provides the use of an antibody or fragment thereof that binds to human AMH for the manufacture of a medicament for use in a method of inhibiting growth of tumor cells of breast cancer and/or of tumor cells of organs of the male and female reproductive systems comprising contacting the tumor cells with the antibody or fragment thereof.

Exemplary cancers or tumor cells to be treated with the methods of the present invention include cancers selected from the group consisting of breast cancer such as e.g. hormone receptor-positive, hormone receptor-negative, triple-negative breast cancer and/or metastatic breast cancer, and cancer of organs of the male and female reproductive systems. Preferably the cancer is selected from the group consisting of cancers of organs of the male and female reproductive systems. More preferably the cancer is selected from the group consisting of ovarian cancer such as e.g. epithelial ovarian cancer (cell types: serous, mucinous and endometrioid), germ cell ovarian cancer and/or sex cord stromal ovarian cancer; fallopian tube cancer; uterine cancer such as e.g. endometrial cancer; cervical cancer such as e.g. all cervical neoplasias, especially squamous cell carcinoma and adenocarcinoma; vaginal cancer; prostate cancer such as e.g. small cell carcinoma and prostate-specific antigen (PSA)-positive tumours; penile cancer; testicular cancer such as e.g. germ cell tumours like seminomas, embryonal carcinomas, teratomas, yolk sac tumours and/or choriocarcinomas and gonadal stromal tumours; metastatic ovarian cancer; and metastatic prostate cancer. Most preferably the cancer is ovarian cancer and/or metastatic ovarian cancer, in particular ovarian cancer selected from the group consisting of epithelial ovarian cancer (cell types: serous, mucinous and endometrioid), germ cell ovarian cancer and/or sex cord stromal ovarian cancer, more particular epithelial ovarian cancer.

In one embodiment, the antibodies of the invention can be used to inhibit or block AMH function which, in turn, can be linked to the prevention or amelioration of certain disease symptoms, thereby implicating AMH as a mediator of the disease. In another embodiment, the antibodies of the invention can be used to purify AMH via immunoaffinity purification.

As previously described, anti-AMH antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation or chemotherapy.

For administration of the antibody, the dosage ranges from about 0.0001 to 100 mg/kg, and more usually 0.01 to 10 mg/kg, of the host body weight. An exemplary treatment regime entails administration once daily, every second day, twice per week, once per week, once every two weeks, once every three weeks, once every four weeks, once a month, once every 3 months or once every three to 6 months. The antibody is usually administered on multiple occasions. Intervals between single dosages can be, for example, daily, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. Alternatively, antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

Actual dosage levels of the active ingredients, i.e. the antibody in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

In certain embodiments of the invention, it may be desirable to use an antibody fragment, rather than an intact antibody, for example, to increase tissue or tumor penetration. It may also be desirable to modify the antibody fragment in order to increase its serum half-life. This may be achieved by incorporation of a salvage receptor binding epitope into the antibody fragment, for example, by mutation of the appropriate region in the antibody fragment or by incorporating the epitope into a peptide tag that is then fused to the antibody fragment at either end or in the middle, for example, by DNA or peptide synthesis (see, e.g., WO96/32478).

"Therapeutically effective amount" or "effective amount", which are used synonymously herein, refer to an amount of the anti-AMH antibodies described herein effective to ameliorate or prevent the symptoms, or prolong the survival of the subject being treated. Determination of a therapeutically effective amount is well within the capabilities of those skilled in the art, especially in light of the detailed disclosure provided herein. The term "therapeutically effective amount" of the anti-AMH antibodies described herein specifically refers to the amount needed to delay or inhibit tumor growth. A "therapeutically effective amount" of an anti-AMH antibody of the invention preferably results in a decrease in severity of disease symptoms, an increase in frequency and duration of disease symptom-free periods, and/or a prevention of impairment or disability due to the disease affliction. For example, for the treatment of cancer, a "therapeutically effective amount" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The antibody or the composition of the present invention can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion. More preferred routes of administration are intravenous or intraperitoneal. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, for example, intranasally, orally, vaginally, rectally, sublingually or topically.

Article of Manufacture and Kit

In another embodiment of the disclosure, an article of manufacture comprising the antibody or fragment thereof, the composition or the immunoconjugate of the invention for the treatment of cancer is provided. The article of manufacture may comprise a container and a label or package insert on or associated with the container. Suitable containers include, for example, bottles, vials or syringes. The containers may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the antibody described herein. The label or package insert may indicate that the composition may be used for treating the condition of choice, such as cancer. Moreover, the article of manufacture may comprise (a) a first container with a composition contained therein, wherein the composition comprises the antibody herein, and (b) a second container with a composition contained therein, wherein the composition comprises a therapeutic agent other than the antibody. The article of manufacture in this embodiment of the disclosure may further comprise a package insert indicating that the first and second compositions can be used in combination to treat cancer. Such therapeutic agent may be any of the adjunct therapies described in the preceding section (e.g., a thrombolytic agent, an anti-platelet agent, a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits comprising the antibody, the compositions or the immunoconjugates of the invention and instructions for use. The kit can further contain one ore more additional reagents, such as an immunosuppressive reagent, a cytotoxic agent or a radiotoxic agent, or one or more additional antibodies of the invention (e.g., a antibody having a complementary activity which binds to an epitope in the AMH antigen distinct from the first antibody).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1: Generation of AMH-Specific Monoclonal Antibodies

Animal care and experiments were performed in accordance with the guidelines for the care and use of laboratory animals of Brandenburg county. AMH-specific monoclonal antibodies (mAb) were generated by hybridoma technology (G. Köhler and C. Milstein "Continuous cultures of fused cells secreting antibody of predefined specificity," Nature. 256, 495-7, 1975). For this purpose 25 weeks old female Balb/c mice were immunized three times with recombinant yeast-expressed His-tagged full-length AMH comprising amino acids 26-560 of human AMH as shown in SEQ ID NO: 10 (Antikörper Online, Aachen, Germany, ABIN2524475). Immunization started with 100 µg recombinant protein using Freund's complete adjuvant. Booster immunizations were carried out five and eight weeks after the first immunization using 50 µg protein without adjuvant. Four days after the final booster immunization electrofusion of spleen cells with myeloma cells (P3X63Ag8.653, ATCC CRL-1580) in the presence of polyethylene glycol 8000 was performed as described (Schenk J. A. et al. "Interleukin 4 increases the antibody response against Rubisco in mice", In Vivo 18, 649-52, 2004). Selected hybrids were cultivated in RPMI 1640 medium (containing 10% FCS, 2 mM glutamine and 50 mM β-mercaptoethanol) and subcloned by limiting dilution on mouse peritoneal feeder cells. Culture supernatants of clones and subclones were tested in an indirect enzyme immunoassay (ELISA) for antigen binding on recombinant AMH adsorbed to microtiter plates (5 µg/ml in PBS). The class and subclass of mAbs were determined in another indirect ELISA. In brief, recombinant AMH (5 µg/ml in PBS) was adsorbed to a microtiter plate. After blocking with PBS/5% NCS (Neonatal calf serum, Biochrom, Berlin, Germany) the culture supernatant of the mAb was added to the plate. After incubation for one hour, biotinylated class- and subclass-specific antibodies (Serva, Heidelberg, Germany) were added, followed by streptavidin-horseradish peroxidase (HRP) conjugate. Staining was done by addition of 3,3',5,5'-Tetramethylbenzidine (TMB). Reaction was stopped after 10 min and absorption measured at 450 nm. The cross reactivity of all antibodies was tested against other His-tagged or yeast expressed proteins (Daskalow K. et al. "Generation of an Antibody against the Protein Phosphatase 1 Inhibitor KEPI and Characterization of the Epitope", Anticancer Research, 30: 1573-1578., 2010; Lawatscheck R. et al. "Chimeric polyomavirus-derived virus-like particles: The immunogenicity of an inserted peptide applied without adjuvant to mice depends on its insertion site and its flanking linker sequence", Viral Immunology 20 (3): 453-460, 2007).

The antibodies were then purified from the hybridoma cell culture supernatants via protein A affinity chromatography to avoid contamination with secretory leucocyte protease inhibitor (J Schenk J. A. et al., "Secretory leukocyte protease inhibitor (SLPI) might contaminate murine monoclonal antibodies after purification on protein G", Journal of Biotechnology 158, 34-35, 2012).

Sandwich Immunoassy (ELISA)

All antibodies were biotinylated using (+) Biotin-N-succinimidyl ester (Fluka, Munich, Germany). To evaluate which antibodies could be used to build up pairs, all possible monoclonal antibody combinations were used for sandwich immunoassay. One antibody (5 µg/ml in PBS) was immobilized overnight in a 96 well plate, respectively. After blocking with PBS/5% NCS, AMH (starting from 500 ng/ml in PBS/NCS) was added for one hour. Then all biotinylated antibodies (~1 µg/ml in PBS/NCS) were added, incubated for one hour and afterwards streptavidin-HRP conjugate (1 µg/ml, Sigma, Munich, Germany) and TMB was added. The reaction was stopped after 20 minutes with sulphuric acid and the absorption measured at 450 nm.

Surface Plasmon Resonance Measurements

Surface-plasmon-resonance (SPR) measurements were performed using a Biacore T200 facility, control software version 2.0, and Series S sensor-chips carboxymethyl dextran chip type 5 (CMS, GE Healthcare Bio-Sciences AB, Uppsala, Sweden). The system was operating at 25° C. in running buffer HBSP (10 mmol/L 4-(2-hydroxyethyl)piperazine-1-ethanesulfonic acid (Hepes), 150 mmol/L NaCl., 0.05% Tween 20, pH 7.4). AMH was transferred to 10 mmol/L sodium acetate buffer pH 4.0 by passing it through a NAPS column (GE Healthcare) before immobilization by amine coupling (Biacore Sensor Surface Handbook). The carboxyl groups on the chip were activated with an mixture containing 200 mM 1-ethyl-3-(3-dimethylaminopropyl)-carbodiimide hydrochloride (EDC, Sigma-Aldrich) and 50 mM N hydroxysuccinimide (NHS, Fluka) for 180 s. AMH was then injected for 150 s at a concentration of 2.5 µg/mL in, at a flow of 10 µL/min and 3 min AMH injection. Approximately 100 resonance units (RU) of AMH were covalently bound to the flow cell. Unreacted NHS esters were blocked with 1 mol/L ethanolamine pH 8.5 for 7 min. Kinetic assays were run at a flow of 30 µL/min for 180 s followed by a 300 s dissociation phase, with antibody concentrations ranging from 0.39 to 200 nmol/L. The sensor surface was regenerated with a 1 min pulse of 100 mmol/L Glycine-HCl pH 1.8. Binding curves were corrected by subtraction of control curves (flowcell 1 without immobilized antigen) and then by subtraction of buffer-injection curves. Association and dissociation rates and the binding constants of the antibodies were determined using the bivalent-analyte-binding model of the Biacore evaluation software (version 2.0). The resulting constants describe the paratope-epitope binding.

Results and Discussion

Immunization of Balb/c mice with AMH led to a titer of about 1:25.000 in the serum when tested on recombinant AMH. Fusion of the spleen cells with myeloma cells resulted in the growth of about 5.000 hybridoma clones. When tested in indirect ELISA, 29 clones produced AMH binding antibodies. Out of these clones, seven hybridoma cell lines were selected, recloned by limited dilution and further characterized. All monoclonal antibodies, G170-AG12, -DA4, -DG11, -DG3, -FC1, -FC5 and -HA12, belonged to the IgG1 isotype and showed no cross reactivity to other His-tagged or yeast expressed proteins. In a sandwich immunoassay with recombinant AMH G170-FC5/G170-HA12-Biotin and G170-DG11/G170-FC5-Biotin gave the strongest results. We were able to detect about 20 ng/ml AMH. Affinity measurements using SPR led to a $K_D$ value of about 1 nm for antibody G170-FC5. According to the SPR measurements, the affinity of all antibodies were ranked FC5>HA12>FC1>DG11>DA4>AG12>DG3. Therefore, G170-FC5 was chosen for further experiments.

Example 2: Cloning and Sequencing of the VH and VL Chains of the Anti-AMH Antibodies from Hybridoma Cell Line G170-FC5

In brief, sequence determination of the hybridoma derived murine antibody was performed according to Toleikis and Frenzel 2012 (doi: 10.1007/978-1-61779-974-7_3). For each positively selected hybridoma clone, total RNA was prepared, reverse-transcribed into cDNA and VH and VL genes were respectively amplified by PCR. These PCR products were ligated into a rescue-vector (pJet1.2, CloneJET PCR Cloning Kit; ThermoFisher Scientific, Cat. No. K1232), allowing for the DNA sequencing of individual PCR products and the determination of mono- or polyclonality of the selected hybridomas. Successful insertion of amplified VH and VL genes was checked by colony PCR. Recombinant plasmids from positive bacterial clones were prepared and sequenced using standard DNA sequencing primers specific for the vector backbone (pJET1.2rev, pJET1.2for). DNA sequences were finally subcloned into an expression vector for recombinant expression of the antibody of interest in mammalian cells.

RNA Isolation

Total RNA was isolated from 2-10×10$^6$ cells using the TRIzol® RNA Isolation reagent (ThermoFisher Scientific, Cat. No. 15596018) according to the manufacturer's protocol; samples were quantified using a NanoDrop ND-1000 spectrophotometer (VWR, Radnor Pa., USA).

One Step RT-PCR

The total RNA preparations described above were further reverse-transcribed into cDNA, and the VH and VL fragments were amplified by PCR using two different mixtures of degenerated primers, each one allowing the recovery of all the different subfamilies of mouse immunoglobulin heavy chain variable fragments and variable heavy chain junction regions or the recovery of all mouse immunoglobulin light chain kappa variable fragments and variable light chain kappa junction regions. The primers used for reverse transcription and amplification (Table 1 and Table 2) were synthesized by Biolegio (Nijmwegen, The Netherlands). Amplification of Fv genes were done according to following protocol using a BioRad T100 thermal cycler (BioRad Laboratories, Hercules, Calif., USA):

| | |
|---|---|
| 5 µl | 5 × HF buffer (New England Biolabs) |
| 1 µl | 10 µM dNTP mix |
| 0.3 µl | Phusion High-fidelity DNA polymerase (New England Biolabs, Cat. No. M0530L) |
| 0.5 µl | cDNA |
| 17.2 µl | H$_2$O |

PCR Program:

| 95° C. | 5 min |
|---|---|

30 Cycles:

| 94° C. | 45 s |
|---|---|
| 54° C. | 45 s |
| 72° C. | 90 s |

Final Elongation:

| 72° C. | 5 min |
|---|---| pJet1.2 Cloning

PCR products were run onto 1.2% (w/v) agarose gels. Following DNA electrophoresis, the fragments of interest (~450 bp) were directly used for cloning cloned into the rescue-vector described above (pJet1.2, CloneJET PCR Cloning Kit; ThermoFisher Scientific, Cat. No. K1232) and transformed into the *E. coli* XL1Blue MRF' strain (Agilent Technologies, Santa Clara, Calif., USA; Cat. No. 200230)

Miniprep Extraction

Positive colonies were cultured overnight at 37° C. in 5 mL of 2×YT medium supplemented with 100 µg/ml ampicillin. The next day plasmid DNA extractions were performed using the NucleoSpin Plasmid EasyPure kit (Macherey-Nagel, Dueren, Geramy; Cat. No. 740727.250).

Sequencing and Sequence Analysis

Samples were sent for DNA sequencing to the DNA sequencing service company LGC (Berlin, Germany). The primers: pJET1.2rev and pJET1.2for (Table 3). To analyse the DNA sequences, vbase2 (doi: 10.1093/nar/gki088) and the ugene bioinformatics software (Unipro, 10.1093/bioinformatics/bts091) were used.

Cloning of Expression Vector for Recombinant Chimeric Antibody Expression

For recombinant expression in mammalian cells, the isolated murine VH and VL gene fragments were formatted as chimeric immunoglobulins by cloning them into YUMAB human IgG expression vectors. Chimeric antibodies consist of a heavy chain where the murine heavy chain variable domain is fused to the human IgG1 heavy chain constant domains (γ1, hinge, γ2, and γ3 regions) and a light chain where the murine light chain variable domain is fused to a human kappa constant domain (Cκ). For protein production of the immunoglobulin candidates, equal quantities of heavy and light chain vector DNA were co-transfected into suspension-adapted HEK-293 cells. Cell culture supernatant was collected after five days and purified using Protein A affinity purification (MabSelect SuRe, GE Healthcare, Cat. No. 17-5438-01)

TABLE 1 primer Mix VH

| heavy chain constant domain: | |
|---|---|
| MHC.F | 5'- GGCCAGTGGATAGTCAGATGGGGGTGTCGTTTTGG C - 3' (SEQ ID NO: 11) |

| heavy chain variable domain | |
|---|---|
| MHV.B1 | 5'- GATGTGAAGCTTCAGGAGTC - 3' (SEQ ID NO: 12) |

TABLE 1-continued primer Mix VH

| | | |
|---|---|---|
| MHV.B2 | 5'- CAGGTGCAGCTGAAGGAGTC - 3' | (SEQ ID NO: 13) |
| MHV.B3 | 5'- CAGGTGCAGCTGAAGCAGTC - 3' | (SEQ ID NO: 14) |
| MHV.B4 | 5'- CAGGTTACTCTGAAAGAGTC - 3' | (SEQ ID NO: 15) |
| MEIV.B5 | 5'- GAGGTCCAGCTGCAACAATCT - 3' | (SEQ ID NO: 16) |
| MHV.B6 | 5'- GAGGTCCAGCTGCAGCAGTC - 3' | (SEQ ID NO: 17) |
| MHV.B7 | 5'- CAGGTCCAACTGCAGCAGCCT - 3' | (SEQ ID NO: 18) |
| MHV.B8 | 5'- GAGGTGAAGCTGGTGGAGTC - 3' | (SEQ ID NO: 19) |
| MHV.B9 | 5'- GAGGTGAAGCTGGTGGAATC - 3' | (SEQ ID NO: 20) |
| MHV.B10 | 5'- GATGTGAACTTGGAAGTGTC - 3' | (SEQ ID NO: 21) |
| MHV.B12 | 5'- GAGGTGCAGCTGGAGGAGTC - 3' | (SEQ ID NO: 22) |

TABLE 2 primer Mix VL

| Kappa chain constant domain | | |
|---|---|---|
| MKC.F | 5'- GGATACAGTTGGTGCAGCATC - 3' | (SEQ ID NO: 23) |

| Kappa chain variable domain | | |
|---|---|---|
| MKV.B1 | 5'- GATGTTTTGATGACCCAAACT -3' | (SEQ ID NO: 24) |
| MKV.B2 | 5'- GATATTGTGATGACGCAGGCT - 3' | (SEQ ID NO: 25) |
| MKV.B3 | 5'- GATATTGTGATAACCCAG - 3' | (SEQ ID NO: 26) |
| MKV.B4 | 5'- GACATTGTGCTGACCCAATCT - 3' | (SEQ ID NO: 27) |
| MKV.B5 | 5'- GACATTGTGATGACCCAGTCT - 3' | (SEQ ID NO: 28) |
| MKV.B6 | 5'- GATATTGTGCTAACTCAGTCT - 3' | (SEQ ID NO: 29) |
| MKV.B7 | 5'- GATATCCAGATGACACAGACT - 3' | (SEQ ID NO: 30) |
| MKV.B8 | 5'- GACATCCAGCTGACTCAGTCT - 3' | (SEQ ID NO: 31) |
| MKV.B9 | 5'- CAAATTGTTCTCACCCAGTCT - 3' | (SEQ ID NO: 32) |
| MKV.B10 | 5'- GACATTCTGATGACCCAGTCT - 3' | (SEQ ID NO: 33) |

TABLE 3 sequencing primers

| | |
|---|---|
| pJET1.2for | CGACTCACTATAGGGAGAGCGGC (SEQ ID NO: 34) |
| pJET1.2rev | AAGAACATCGATTTTCCATGGCAG (SEQ ID NO: 35) |

Antibody Sequences

Heavy Chains

After sequencing, variable heavy chain and variable light chain sequences were analysed using vbase2 bioinformatic tool and ugene software. Functional variable heavy and light chains obtained are displayed below. Complementary determining regions (CDRs) are underlined. Numbering is done according to Kabat E A et al., (1991) Sequences of proteins of immunological interest. 5th Edition—US Department of Health and Human Services, NIH publication no 91-3242.

Functional variable heavy chain G170_FC5_VH_B8
(SEQ ID NO: 7)

EVKLVESGGGLVKPGGSLKLSCAASGFIFS<u>TYTMS</u>WVRQTPGKRLEWVA<u>T</u>

<u>ISSGGSYTYYPDSVKG</u>RFTISRDNAKNTLYLQMSSLRSEDTAMYYCTR<u>HG</u>

<u>SDYRYDGFDY</u>WGQGTTLTVSS

Functional variable light chain G170_FC5_VL_B10
(SEQ ID NO: 8)

DILMTQSPASLSVSVGETVTITC<u>RASENIYSNLA</u>WYQQKQGKSPQLLVY<u>A</u>

<u>ATNLADG</u>VPSRFSGSGSGTQYSLKINSLQSEDFGSYYC<u>QHFWGTPFT</u>FGS

GTKLEIK

Example 3: Evaluation of Tumor Growth Inhibition of Anti-AMH Antibodies in Immunodeficient NMRI Nude Mice Bearing Ovcar-3 Cells Study Objectives The study was designed to test the antitumor effect (survival) of antibody anti-AMH G170-FC5 in the human ovarian carcinoma xenograft Ovcar-3 in female NMRI nu/nu mice.

Description of Studies 20 female NMRI nu/nu mice bearing Ovcar-3 cells were treated according to table 4.

TABLE 4

Summary of treatment

| Group | No. mice | Substance | Route | Dose (μg/mouse/inj.) | Sequence | Deaths (days) | BW gain [%] compared to d 19 (day) | median survival [days] |
|---|---|---|---|---|---|---|---|---|
| A | 10 | Vehicle | i.p. | — | daily | 9 | +26.0 | 20 |
| B | 5 | anti-AMH | i.p. | 1.5 | daily | 3 | +15.2 | 22 |
| C | 5 | anti-AMH | i.p. | 15 | daily | 3 | +15.1 | 28 |

Body weight was measured three times per week. Autopsy was performed on sacrificed mice. Animals had to be sacrifed if body weight change was above 120% or animals were in a bad health condition. The solution anti-AMH antibody (1.23 mg/ml) was diluted for application to 0.15 μg/ml and 1.5 μg/ml in 0.9% NaCl. The solution was prepared before use. 10 ml/kg solution was applied i.p. Studyplan overview and treatment groups is provided by table 5 and compounds used by table 6.

TABLE 5

Studyplan overview and treatment groups

| Animals: | Mice | Animal age: | 6 weeks | Total number of animals: | | 20 | Sex: | female |
|---|---|---|---|---|---|---|---|---|
| Groups: | Strain: | Tumour/Cells | Origin | Cell count: | Side | Day: | | Sterile assay |
| A-C | NMRI nu/nu | Ovcar-3 (P24) | in vitro | 3.4 × 10^6 | i.p. | 0 | | — |

| | Parameters: | Body weight | Survival | Tumour volume | Others: |
|---|---|---|---|---|---|
| Groups: | all | X 3x/week | x daily | — | — |

Test cpd: see Table 3

| Group | n | Treatment | Application | Treatment Days | Dose (μg/mouse/inj.) |
|---|---|---|---|---|---|
| A | 10 | Vehicle | i.p. | daily | |
| B | 5 | anti-AMH antibody | i.p. | daily | 1.5 from d 4 on |
| C | 5 | anti-AMH antibody | i.p. | daily | 1.5 d 4-10, 15 g from d 11 on |

TABLE 6

Compounds used

| | Compound Description | | | Stor- | Description of |
|---|---|---|---|---|---|
| Group | Treatment | Origin | Charge(Lot) | age | formulation |
| A | 0.9% NaCl | Braun | n/a | 4° C. | |
| B + C | anti-AMH antibody | HybroTec | 3 × 1 ml | 4° C. | 1.23 mg/ml (anti-AMH G170-FC5) diluted with 0.9% NaCl |

Summary of Results

Figure 2:
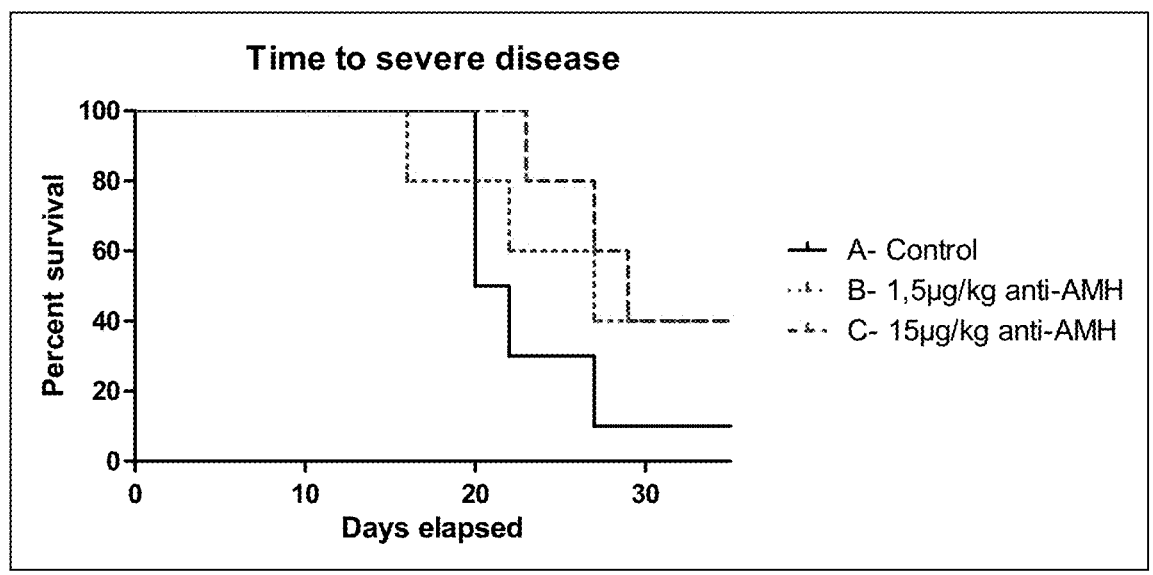
FIG. 2 shows Kaplan-Meier survival curve of mice bearing Ovcar-3 cells treated with anti-AMH antibody.

On day 16 (12 days after treatment start) the first mouse (B3) had to be sacrificed. The untreated group A had a median survival of 20 days. Treatment with 1.5 μg/injection anti-AMH antibody daily for up to 47 days resulted in a median survival of 22 days. The treatment with 1.5 μg/injection from d4-10 and 15 μg/injection from day 11 on resulted in a median survival of 28 days. Mice showed influence on body weight change due to the creation of ascites. Control group A showed slightly stronger body weight increase compared to treated groups (FIG. 1). No toxic effects were seen. Treatment with either 1.5 μg or 15 μg anti-AMH daily i.p. prolonged time to severe disease ($p=0.251$ and $p=0.092$) compared to the control group (FIG. 2). The autopsy of all groups revealed alterations in most of the mice: mice had strong metastasis and bloody or cloudy ascites.

CONCLUSION

Anti-AMH antibody showed prolonged time to severe disease compared to the vehicle treated control group in the Ovcar-3 xenograft model. 4/10 mice did not developed ascites, but metastasis. The body weight change showed an earlier increase of body weight due to an early production of ascites in the vehicle treated control group. Increasing the dose from 15 μg might strengthen the efficacy of the antibody.

Example 4: Evaluation of Tumor Growth Inhibition of Anti-AMH Antibodies in the Human Ovarian Carcinoma Patient-Derived Xenograft Ov13451B in Female NMRI Nu/Nu Mice Study Objectives The study was designed to test the antitumor effect (survival) of antibody anti-AMH G170-FC5 in the human ovarian carcinoma patient-derived xenograft Ov13451B in female NMRI nu/nu mice.

Description of Studies 10 female NMRI nu/nu mice were subcutaneously inoculated with Ov13451B fragments at day 0 and were treated starting one day before tumor inoculation according to table 7. Ov13451B fragments were obtained by cutting pieces of 2-3 mm×2-3 mm of patient derived ovarian tumor.

TABLE 7

Summary of treatment

| Group | No. mice | Substance | Route | Dose (μg/mouse/inj.) | Sequence starting d −1 | Deaths (days) |
|---|---|---|---|---|---|---|
| A | 5 | Vehicle | i.p. | — | Daily | 0 |
| B | 5 | anti-AMH | i.p. | 30 | Daily | 0 |

Tumor volume and body weight was measured two times per week. Autopsy was performed on sacrificed mice. Animals had to be sacrifed if tumor volume was above 1 cm³ or animals were in a bad health condition.

The solution anti-AMH antibody (1 mg/ml) was diluted for application to 3 μg/ml in 0.9% NaCl. The solution was prepared before use. 10 ml/kg solution was applied i.p. Studyplan overview and treatment groups are provided by table 8 and compounds used by table 9.

TABLE 8

Studyplan overview and treatment groups

| Animals: | Mice | Animal age: | 6 weeks | Total number of animals: | 20 | Sex: | Female |
|---|---|---|---|---|---|---|---|
| Groups: | Strain: | Tumour/Cells Origin | | Cell count: | Side | Day: | Sterile assay |
| A-B | NMRI nu/nu | Ov13541B (P3) | in vivo | 3 × 3 mm | s.c. | 0 | — |

| | Parameters: | Body weight | Survival | Tumour volume |
|---|---|---|---|---|
| Groups: | all | x 2x/week | x daily | x 2x/week |

| | Test cpd: | see Table 9 |
|---|---|---|
| | Remarks: | Therapy start 1 day before tumor transplantation End of experiment: when individual mouse has signs of large tumors (+10% BW), or large ascites volumes or moribund Autopsy: weight of all tumors/mouse; Serum 1x/week |

| Group | N | Treatment | Application | Treatment Days | Dose (μg/mouse/inj.) |
|---|---|---|---|---|---|
| A | 5 | Vehicle | i.p. | daily | |
| B | 5 | anti-AMH antibody | i.p. | daily | 30 μg |

TABLE 9

Compounds used

| | | Compound Description | | Stor- | Description of |
|---|---|---|---|---|---|
| Group | Treatment | Origin | Charge(Lot) | age | formulation |
| A | 0.9% NaCl | Braun | n/a | 4° C. | |
| B | anti-AMH antibody | HybroTec | 1 × 8 ml | 4° C. | 1 mg/ml (anti-AMH G170-FC5) diluted with 0.9% NaCl |

TABLE 10

Tumor volume values [cm³]

| | | Day | | | | | | | |
|---|---|---|---|---|---|---|---|---|---|
| Group | | 0 | 2 | 5 | 8 | 13 | 16 | 19 | 22 |
| A-Vehicle | A1 | 0.014 | 0.014 | 0.329 | 0.355 | 0.345 | 0.354 | 0.323 | 0.294 |
| | A2 | 0.014 | 0.014 | 0.242 | 0.267 | 0.321 | 0.450 | 0.542 | 0.816 |
| | A3 | 0.014 | 0.014 | 0.116 | 0.285 | 0.296 | 0.375 | 0.376 | 0.387 |

TABLE 10-continued

| | | Tumor volume values [cm³] | | | | | | | |
|---|---|---|---|---|---|---|---|---|---|
| | | Day | | | | | | | |
| Group | | 0 | 2 | 5 | 8 | 13 | 16 | 19 | 22 |
| | A4 | 0.014 | 0.014 | 0.174 | 0.197 | 0.207 | 0.282 | 0.248 | 0.271 |
| | A5 | 0.014 | 0.014 | 0.193 | 0.243 | 0.251 | 0.297 | 0.248 | 0.270 |
| B -anti-AMH | B1 | 0.014 | 0.014 | 0.004 | 0.004 | 0.004 | 0.001 | 0.001 | 0.001 |
| (30 µg/mouse) | B2 | 0.014 | 0.014 | 0.110 | 0.190 | 0.282 | 0.541 | 0.549 | 0.606 |
| | B3 | 0.014 | 0.014 | 0.098 | 0.197 | 0.201 | 0.200 | 0.208 | 0.191 |
| | B4 | 0.014 | 0.014 | 0.114 | 0.202 | 0.241 | 0.287 | 0.357 | 0.419 |
| | B5 | 0.014 | 0.014 | 0.004 | 0.001 | 0.001 | 0.001 | 0.001 | 0.001 |

Summary of Results

Figure 3:
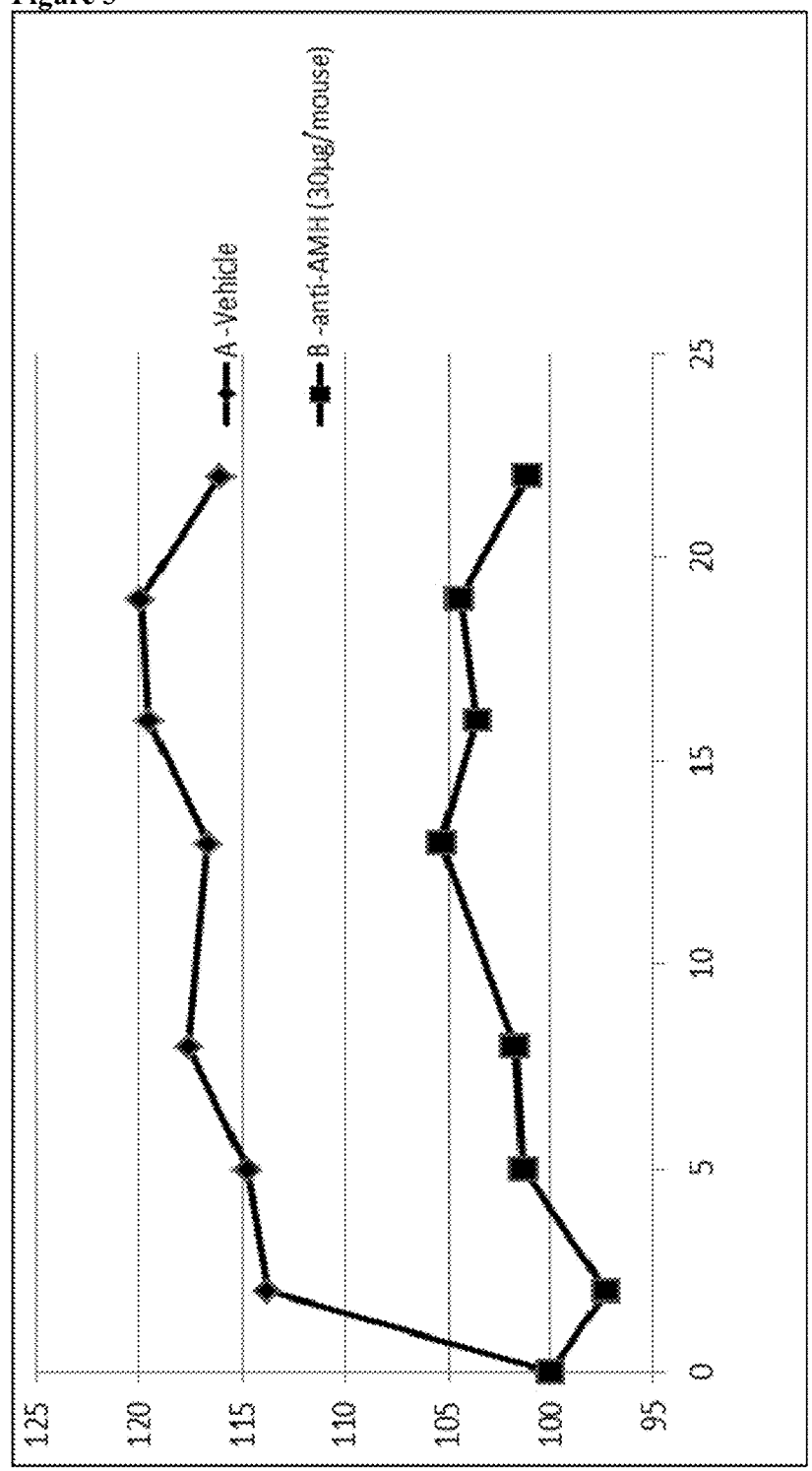
FIG. 3 shows body weight change [%] of human ovarian carcinoma patient-derived xenograft Ov13451B mice treated with anti-AMH antibody.
Figure 4:
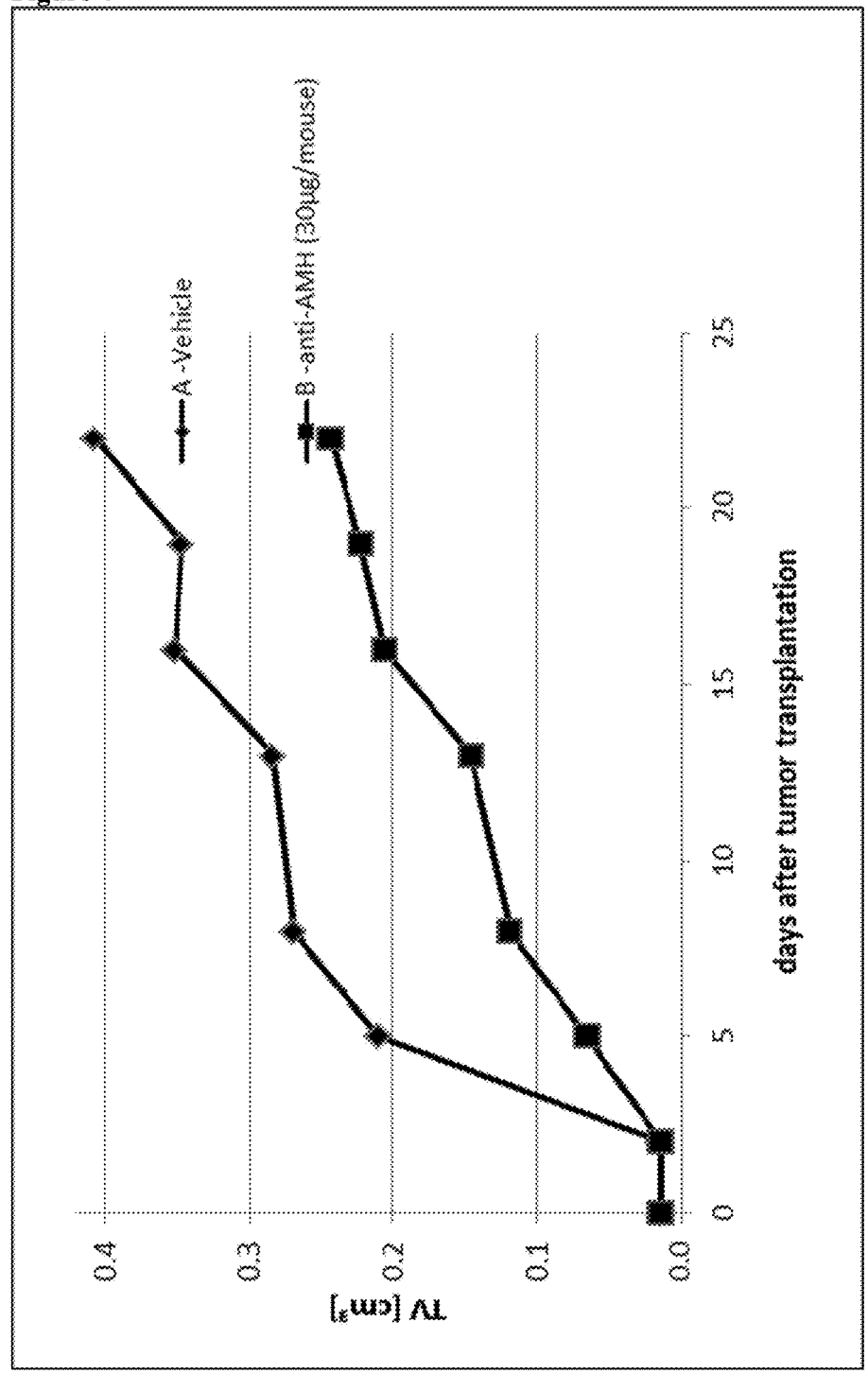
FIG. 4 shows tumor growth curve as mean tumor volume [cm$^3$] of human ovarian carcinoma patient-derived xenograft Ov13451B mice treated with anti-AMH antibody.

Mice tolerated 30 µg/mouse of anti-AMH daily very well. Control group A showed slightly stronger body weight increase compared to treated groups (FIG. 3). No toxic effects were seen. On day 22 the untreated group A had a mean tumor volume of 408 mm³. The treatment with 30 µg/injection from d-1 resulted in a mean TV of 244 mm³ (table 10 and FIG. 4).

CONCLUSION

Anti-AMH antibody showed a slight inhibition of tumor growth onset from day 0 to 8 after tumor inoculation as well as a slower tumor growth until day 22 compared to the vehicle treated control group in the Ov13451B xenograft model. 2/5 mice of anti-AMH treated mice did not develop tumors. Increasing the dose from 30 µg might strengthen the efficacy of the antibody.

The invention claimed is:

1. A method for treating cancer in a subject comprising administering to the subject in need of thereof an antibody or fragment thereof that binds to human Anti-Müllerian hormone (AMH), wherein the cancer is selected from the group consisting of breast cancer and cancer of organs of the male and female reproductive systems, wherein the antibody or fragment thereof that binds to AMH comprises a heavy chain CDR1 comprising the amino acid sequence of SEQ ID NO: 1, and a heavy chain CDR2 comprising the amino acid sequence of SEQ ID NO: 2, and a heavy chain CDR3 comprising the amino acid sequence of SEQ ID NO: 3; and a light chain CDR1 comprising the amino acid sequence of SEQ ID NO: 4, and a light chain CDR2 comprising the amino acid sequence of SEQ ID NO: 5, and a light chain CDR3 comprising the amino acid sequence of SEQ ID NO: 6.

2. The method of claim 1, wherein the cancer is selected from the group consisting of cancer of organs of the male and female reproductive systems.

3. The method of claim 2, wherein the cancer of organs of the male and female reproductive systems is selected from the group consisting of ovarian cancer, fallopian tube cancer, uterine cancer, cervical cancer, vaginal cancer, prostate cancer, penile cancer, testicular cancer, metastatic ovarian cancer, and metastatic prostate cancer.

4. The method of claim 1, wherein the cancer is ovarian cancer and/or metastatic ovarian cancer.

5. A method of inhibiting growth of tumor cells of breast cancer and/or of tumor cells of organs of the male and female reproductive systems, comprising contacting the tumor cells with an antibody or fragment thereof that binds to human Anti-Müllerian hormone (AMH), wherein the antibody or fragment thereof that binds to AMR comprises a heavy chain CDR1 comprising the amino acid sequence of SEQ ID NO: 1, and a heavy chain CDR2 comprising the amino acid sequence of SEQ ID NO: 2, and a heavy chain CDR3 comprising the amino acid sequence of SEQ ID NO: 3; and a light chain CDR1 comprising the amino acid sequence of SEQ ID NO: 4, and a light chain CDR2 comprising the amino acid sequence of SEQ ID NO: 5, and a light chain CDR3 comprising the amino acid sequence of SEQ ID NO: 6.

6. An antibody or fragment thereof that binds to human Anti-Mullerian hormone (AMH), wherein the antibody or fragment thereof comprises a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3; and comprises a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6.

7. The antibody or fragment thereof of claim 6, wherein the antibody or fragment thereof comprises a heavy chain variable region of SEQ ID NO: 7 and/or a light chain variable region sequence of SEQ ID NO: 8.

8. The antibody or fragment thereof of claim 7, wherein the antibody or fragment thereof is a murine antibody or a fragment thereof, a chimeric antibody or a fragment thereof or a humanized antibody or fragment thereof.

9. The antibody or fragment thereof of claim 7, wherein the antibody or fragment thereof binds to human AMH with an affinity ($K_d$) of 10 nM or less.

10. The antibody or fragment thereof of claim 6, wherein the antibody or fragment thereof comprises a heavy chain variable framework region sequence which is at least 90% identical to the framework region sequence of SEQ ID NO: 7 and/or a light chain variable framework region sequence which is at least 90% identical to the framework region sequence of SEQ ID NO: 8.

11. The antibody or fragment thereof of claim 6, wherein the antibody or fragment thereof is a murine antibody or a fragment thereof, a chimeric antibody or a fragment thereof or a humanized antibody or fragment thereof.

12. The antibody or fragment thereof of claim 6, wherein the antibody or fragment thereof binds to human AMH with an affinity ($K_d$) of 10 nM or less.

13. A composition comprising the antibody or fragment thereof of claim 6 and a pharmaceutically acceptable carrier.

* * * * *

SEQUENCE LISTING

```
<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: HCDR1

<400> SEQUENCE: 1

Thr Tyr Thr Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Thr Ile Ser Ser Gly Gly Ser Tyr Thr Tyr Tyr Pro Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: HCDR3
```

<400> SEQUENCE: 3

His Gly Ser Asp Tyr Arg Tyr Asp Gly Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: LCDR1

<400> SEQUENCE: 4

Arg Ala Ser Glu Asn Ile Tyr Ser Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Ala Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gln His Phe Trp Gly Thr Pro Phe Thr
1               5

<210> SEQ ID NO 7
<211> LENGTH: 121
<212> TYPE: PRT
<213> ORGANISM: Mus musculus

<400> SEQUENCE: 7

Glu Val Lys Leu Val Glu Ser Gly Gly Leu Val Lys Pro Gly Gly
1               5                   10                  15

Ser Leu Lys Leu Ser Cys Ala Ala Ser Gly Phe Ile Phe Ser Thr Tyr
                20                  25                  30

Thr Met Ser Trp Val Arg Gln Thr Pro Gly Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Thr Arg His Gly Ser Asp Tyr Arg Tyr Asp Gly Phe Asp Tyr Trp Gly
                100                 105                 110

Gln Gly Thr Thr Leu Thr Val Ser Ser
            115                 120

<210> SEQ ID NO 8
<211> LENGTH: 107

```
<212> TYPE: PRT
<213> ORGANISM: Mus musculus

<400> SEQUENCE: 8

Asp Ile Leu Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Phe
                85                  90                  95

Thr Phe Gly Ser Gly Thr Lys Leu Glu Ile Lys
            100                 105

<210> SEQ ID NO 9
<211> LENGTH: 560
<212> TYPE: PRT
<213> ORGANISM: Homo sapiens

<400> SEQUENCE: 9

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
    130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240
```

```
Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Leu Arg Pro
            340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
    370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Leu Lys Ala Leu Gln
            420                 425                 430

Gly Leu Arg Val Glu Trp Arg Gly Arg Asp Pro Arg Gly Pro Gly Arg
        435                 440                 445

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510

Met Gln Val Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
    530                 535                 540

Ser Ala His His Val Pro Asn Met Val Ala Thr Glu Cys Gly Cys Arg
545                 550                 555                 560

<210> SEQ ID NO 10
<211> LENGTH: 535
<212> TYPE: PRT
<213> ORGANISM: Artificial Sequence
<220> FEATURE:
<223> OTHER INFORMATION: Amino acids 26-560 of human AMH

<400> SEQUENCE: 10

Arg Ala Glu Glu Pro Ala Val Gly Thr Ser Gly Leu Ile Phe Arg Glu
1               5                   10                  15

Asp Leu Asp Trp Pro Pro Gly Ser Pro Gln Glu Pro Leu Cys Leu Val
            20                  25                  30

Ala Leu Gly Gly Asp Ser Asn Gly Ser Ser Ser Pro Leu Arg Val Val
        35                  40                  45
```

-continued

Gly Ala Leu Ser Ala Tyr Glu Gln Ala Phe Leu Gly Ala Val Gln Arg
    50                  55                  60

Ala Arg Trp Gly Pro Arg Asp Leu Ala Thr Phe Gly Val Cys Asn Thr
 65                  70                  75                  80

Gly Asp Arg Gln Ala Ala Leu Pro Ser Leu Arg Arg Leu Gly Ala Trp
                 85                  90                  95

Leu Arg Asp Pro Gly Gly Gln Arg Leu Val Val Leu His Leu Glu Glu
            100                 105                 110

Val Thr Trp Glu Pro Thr Pro Ser Leu Arg Phe Gln Glu Pro Pro
        115                 120                 125

Gly Gly Ala Gly Pro Pro Glu Leu Ala Leu Leu Val Leu Tyr Pro Gly
    130                 135                 140

Pro Gly Pro Glu Val Thr Val Thr Arg Ala Gly Leu Pro Gly Ala Gln
145                 150                 155                 160

Ser Leu Cys Pro Ser Arg Asp Thr Arg Tyr Leu Val Leu Ala Val Asp
                165                 170                 175

Arg Pro Ala Gly Ala Trp Arg Gly Ser Gly Leu Ala Leu Thr Leu Gln
            180                 185                 190

Pro Arg Gly Glu Asp Ser Arg Leu Ser Thr Ala Arg Leu Gln Ala Leu
        195                 200                 205

Leu Phe Gly Asp Asp His Arg Cys Phe Thr Arg Met Thr Pro Ala Leu
    210                 215                 220

Leu Leu Leu Pro Arg Ser Glu Pro Ala Pro Leu Pro Ala His Gly Gln
225                 230                 235                 240

Leu Asp Thr Val Pro Phe Pro Pro Arg Pro Ser Ala Glu Leu Glu
                245                 250                 255

Glu Ser Pro Pro Ser Ala Asp Pro Phe Leu Glu Thr Leu Thr Arg Leu
            260                 265                 270

Val Arg Ala Leu Arg Val Pro Pro Ala Arg Ala Ser Ala Pro Arg Leu
        275                 280                 285

Ala Leu Asp Pro Asp Ala Leu Ala Gly Phe Pro Gln Gly Leu Val Asn
    290                 295                 300

Leu Ser Asp Pro Ala Ala Leu Glu Arg Leu Leu Asp Gly Glu Glu Pro
305                 310                 315                 320

Leu Leu Leu Leu Arg Pro Thr Ala Thr Thr Gly Asp Pro Ala
                325                 330                 335

Pro Leu His Asp Pro Thr Ser Ala Pro Trp Ala Thr Ala Leu Ala Arg
            340                 345                 350

Arg Val Ala Ala Glu Leu Gln Ala Ala Ala Glu Leu Arg Ser Leu
        355                 360                 365

Pro Gly Leu Pro Pro Ala Thr Ala Pro Leu Leu Ala Arg Leu Leu Ala
    370                 375                 380

Leu Cys Pro Gly Gly Pro Gly Leu Gly Asp Pro Leu Arg Ala Leu
385                 390                 395                 400

Leu Leu Leu Lys Ala Leu Gln Gly Leu Arg Val Glu Trp Arg Gly Arg
                405                 410                 415

Asp Pro Arg Gly Pro Gly Arg Ala Gln Arg Ser Ala Gly Ala Thr Ala
            420                 425                 430

Ala Asp Gly Pro Cys Ala Leu Arg Glu Leu Ser Val Asp Leu Arg Ala
        435                 440                 445

Glu Arg Ser Val Leu Ile Pro Glu Thr Tyr Gln Ala Asn Asn Cys Gln
    450                 455                 460

Gly Val Cys Gly Trp Pro Gln Ser Asp Arg Asn Pro Arg Tyr Gly Asn

```
            465                 470                 475                 480
His Val Val Leu Leu Lys Met Gln Val Arg Gly Ala Ala Leu Ala
                485                 490                 495

Arg Pro Pro Cys Cys Val Pro Thr Ala Tyr Ala Gly Lys Leu Leu Ile
            500                 505                 510

Ser Leu Ser Glu Glu Arg Ile Ser Ala His His Val Pro Asn Met Val
            515                 520                 525

Ala Thr Glu Cys Gly Cys Arg
            530             535

<210> SEQ ID NO 11
<211> LENGTH: 36
<212> TYPE: DNA
<213> ORGANISM: Artificial Sequence
<220> FEATURE:
<223> OTHER INFORMATION: PRIMER MHC.F

<400> SEQUENCE: 11
ggccagtgga tagtcagatg ggggtgtcgt tttggc                                 36

<210> SEQ ID NO 12
<211> LENGTH: 20
<212> TYPE: DNA
<213> ORGANISM: Artificial Sequence
<220> FEATURE:
<223> OTHER INFORMATION: PRIMER MHV.B1

<400> SEQUENCE: 12
gatgtgaagc ttcaggagtc                                                   20

<210> SEQ ID NO 13
<211> LENGTH: 20
<212> TYPE: DNA
<213> ORGANISM: Artificial Sequence
<220> FEATURE:
<223> OTHER INFORMATION: PRIMER MHV.B2

<400> SEQUENCE: 13
caggtgcagc tgaaggagtc                                                   20

<210> SEQ ID NO 14
<211> LENGTH: 20
<212> TYPE: DNA
<213> ORGANISM: Artificial Sequence
<220> FEATURE:
<223> OTHER INFORMATION: PRIMER MHV.B3

<400> SEQUENCE: 14
caggtgcagc tgaagcagtc                                                   20

<210> SEQ ID NO 15
<211> LENGTH: 20
<212> TYPE: DNA
<213> ORGANISM: Artificial Sequence
<220> FEATURE:
<223> OTHER INFORMATION: PRIMER MHV.B4

<400> SEQUENCE: 15
caggttactc tgaaagagtc                                                   20

<210> SEQ ID NO 16
<211> LENGTH: 21
<212> TYPE: DNA
<213> ORGANISM: Artificial Sequence
```

```
<220> FEATURE:
<223> OTHER INFORMATION: PRIMER MHV.B5

<400> SEQUENCE: 16
gaggtccagc tgcaacaatc t                                          21

<210> SEQ ID NO 17
<211> LENGTH: 20
<212> TYPE: DNA
<213> ORGANISM: Artificial Sequence
<220> FEATURE:
<223> OTHER INFORMATION: PRIMER MHV.B6

<400> SEQUENCE: 17
gaggtccagc tgcagcagtc                                            20

<210> SEQ ID NO 18
<211> LENGTH: 21
<212> TYPE: DNA
<213> ORGANISM: Artificial Sequence
<220> FEATURE:
<223> OTHER INFORMATION: PRIMER MHV.B7

<400> SEQUENCE: 18
caggtccaac tgcagcagcc t                                          21

<210> SEQ ID NO 19
<211> LENGTH: 20
<212> TYPE: DNA
<213> ORGANISM: Artificial Sequence
<220> FEATURE:
<223> OTHER INFORMATION: PRIMER MHV.B8

<400> SEQUENCE: 19
gaggtgaagc tggtggagtc                                            20

<210> SEQ ID NO 20
<211> LENGTH: 20
<212> TYPE: DNA
<213> ORGANISM: Artificial Sequence
<220> FEATURE:
<223> OTHER INFORMATION: PRIMER MHV.B9

<400> SEQUENCE: 20
gaggtgaagc tggtggaatc                                            20

<210> SEQ ID NO 21
<211> LENGTH: 20
<212> TYPE: DNA
<213> ORGANISM: Artificial Sequence
<220> FEATURE:
<223> OTHER INFORMATION: PRIMER MHV.B10

<400> SEQUENCE: 21
gatgtgaact tggaagtgtc                                            20

<210> SEQ ID NO 22
<211> LENGTH: 20
<212> TYPE: DNA
<213> ORGANISM: Artificial Sequence
<220> FEATURE:
<223> OTHER INFORMATION: PRIMER MHV.B12

<400> SEQUENCE: 22
gaggtgcagc tggaggagtc                                            20
```

<210> SEQ ID NO 23
<211> LENGTH: 21
<212> TYPE: DNA
<213> ORGANISM: Artificial Sequence
<220> FEATURE:
<223> OTHER INFORMATION: PRIMER MKC.F

<400> SEQUENCE: 23
ggatacagtt ggtgcagcat c             21

<210> SEQ ID NO 24
<211> LENGTH: 21
<212> TYPE: DNA
<213> ORGANISM: Artificial Sequence
<220> FEATURE:
<223> OTHER INFORMATION: PRIMER MKV.B1

<400> SEQUENCE: 24
gatgttttga tgacccaaac t             21

<210> SEQ ID NO 25
<211> LENGTH: 21
<212> TYPE: DNA
<213> ORGANISM: Artificial Sequence
<220> FEATURE:
<223> OTHER INFORMATION: PRIMER MKV.B2

<400> SEQUENCE: 25
gatattgtga tgacgcaggc t             21

<210> SEQ ID NO 26
<211> LENGTH: 18
<212> TYPE: DNA
<213> ORGANISM: Artificial Sequence
<220> FEATURE:
<223> OTHER INFORMATION: PRIMER MKV.B3

<400> SEQUENCE: 26
gatattgtga taacccag                 18

<210> SEQ ID NO 27
<211> LENGTH: 21
<212> TYPE: DNA
<213> ORGANISM: Artificial Sequence
<220> FEATURE:
<223> OTHER INFORMATION: PRIMER MKV.B4

<400> SEQUENCE: 27
gacattgtgc tgacccaatc t             21

<210> SEQ ID NO 28
<211> LENGTH: 21
<212> TYPE: DNA
<213> ORGANISM: Artificial Sequence
<220> FEATURE:
<223> OTHER INFORMATION: PRIMER MKV.B5

<400> SEQUENCE: 28
gacattgtga tgacccagtc t             21

<210> SEQ ID NO 29
<211> LENGTH: 21
<212> TYPE: DNA
<213> ORGANISM: Artificial Sequence
<220> FEATURE:
<223> OTHER INFORMATION: PRIMER MKV.B6

```
<400> SEQUENCE: 29
gatattgtgc taactcagtc t                                              21

<210> SEQ ID NO 30
<211> LENGTH: 21
<212> TYPE: DNA
<213> ORGANISM: Artificial Sequence
<220> FEATURE:
<223> OTHER INFORMATION: PRIMER MKV.B7

<400> SEQUENCE: 30
gatatccaga tgacacagac t                                              21

<210> SEQ ID NO 31
<211> LENGTH: 21
<212> TYPE: DNA
<213> ORGANISM: Artificial Sequence
<220> FEATURE:
<223> OTHER INFORMATION: PRIMER MKV.B8

<400> SEQUENCE: 31
gacatccagc tgactcagtc t                                              21

<210> SEQ ID NO 32
<211> LENGTH: 21
<212> TYPE: DNA
<213> ORGANISM: Artificial Sequence
<220> FEATURE:
<223> OTHER INFORMATION: PRIMER MKV.B9

<400> SEQUENCE: 32
caaattgttc tcacccagtc t                                              21

<210> SEQ ID NO 33
<211> LENGTH: 21
<212> TYPE: DNA
<213> ORGANISM: Artificial Sequence
<220> FEATURE:
<223> OTHER INFORMATION: PRIMER MKV.B10

<400> SEQUENCE: 33
gacattctga tgacccagtc t                                              21

<210> SEQ ID NO 34
<211> LENGTH: 23
<212> TYPE: DNA
<213> ORGANISM: Artificial Sequence
<220> FEATURE:
<223> OTHER INFORMATION: PRIMER pJET1.2for

<400> SEQUENCE: 34
cgactcacta tagggagagc ggc                                            23

<210> SEQ ID NO 35
<211> LENGTH: 24
<212> TYPE: DNA
<213> ORGANISM: Artificial Sequence
<220> FEATURE:
<223> OTHER INFORMATION: PRIMER pJET1.2rev

<400> SEQUENCE: 35
aagaacatcg attttccatg gcag                                           24
```